United States Patent [19]

Lehmann et al.

[11] Patent Number: 4,737,357
[45] Date of Patent: Apr. 12, 1988

[54] AQUEOUS COATING DISPERSIONS

[75] Inventors: Klaus Lehmann, Rossdorf; Dieter Dreher, Darmstadt; Wolfgang Weisbrod, Michelstadt, all of Fed. Rep. of Germany

[73] Assignee: Röhm GmbH, Darmstadt, Fed. Rep. of Germany

[21] Appl. No.: 56,291

[22] Filed: May 29, 1987

Related U.S. Application Data

[63] Continuation of Ser. No. 937,430, Dec. 2, 1986, abandoned, which is a continuation of Ser. No. 787,969, Oct. 16, 1985, abandoned.

[30] Foreign Application Priority Data

Oct. 19, 1984 [DE] Fed. Rep. of Germany ....... 3438291

[51] Int. Cl.$^4$ .............................................. A61K 9/32
[52] U.S. Cl. .................... 424/487; 524/547; 524/555; 526/287; 526/292.2; 526/292.95; 424/497
[58] Field of Search .................. 424/33; 524/547, 555; 526/287, 292.2, 292.95

[56] References Cited

U.S. PATENT DOCUMENTS 3,287,305 11/1966 Maeder ........................... 526/292.95
3,520,970 7/1970 Lehmann et al. ..................... 424/25
4,077,930 3/1978 Lim ................................. 526/292.2
4,251,651 2/1981 Kawakami ....................... 526/292.2
4,305,860 12/1981 Iovine ................................ 524/547
4,444,954 4/1984 Mels ................................. 524/555
4,444,955 4/1984 Mels ................................. 524/555
4,452,862 6/1984 Markert et al. ..................... 428/407
4,520,172 5/1985 Lehmann et al. ................... 525/369
4,548,981 10/1985 Kolesinski ......................... 524/555
4,617,362 10/1986 Becker ............................. 526/292.2

FOREIGN PATENT DOCUMENTS 0058765 9/1982 European Pat. Off. ............ 428/407
0088951 9/1983 European Pat. Off. ............ 525/369
3208791 3/1971 Fed. Rep. of Germany .
1617751 1/1985 Fed. Rep. of Germany .

Primary Examiner—Paul R. Michl
Assistant Examiner—Patrick A. Doody
Attorney, Agent, or Firm—Curtis, Morris & Safford

[57] ABSTRACT

Aqueous dispersions of a water-swellable but water-insoluble polymer formed between a quaternary ammonium monomer and a nonionic monomer; methods for making such dispersions by dispersing said copolymers, in the form of a powder, in water; methods for coating pharmaceutical cores, powders, or granules with such dispersions; and coated pharmaceutical products made by such methods.

3 Claims, 1 Drawing Sheet

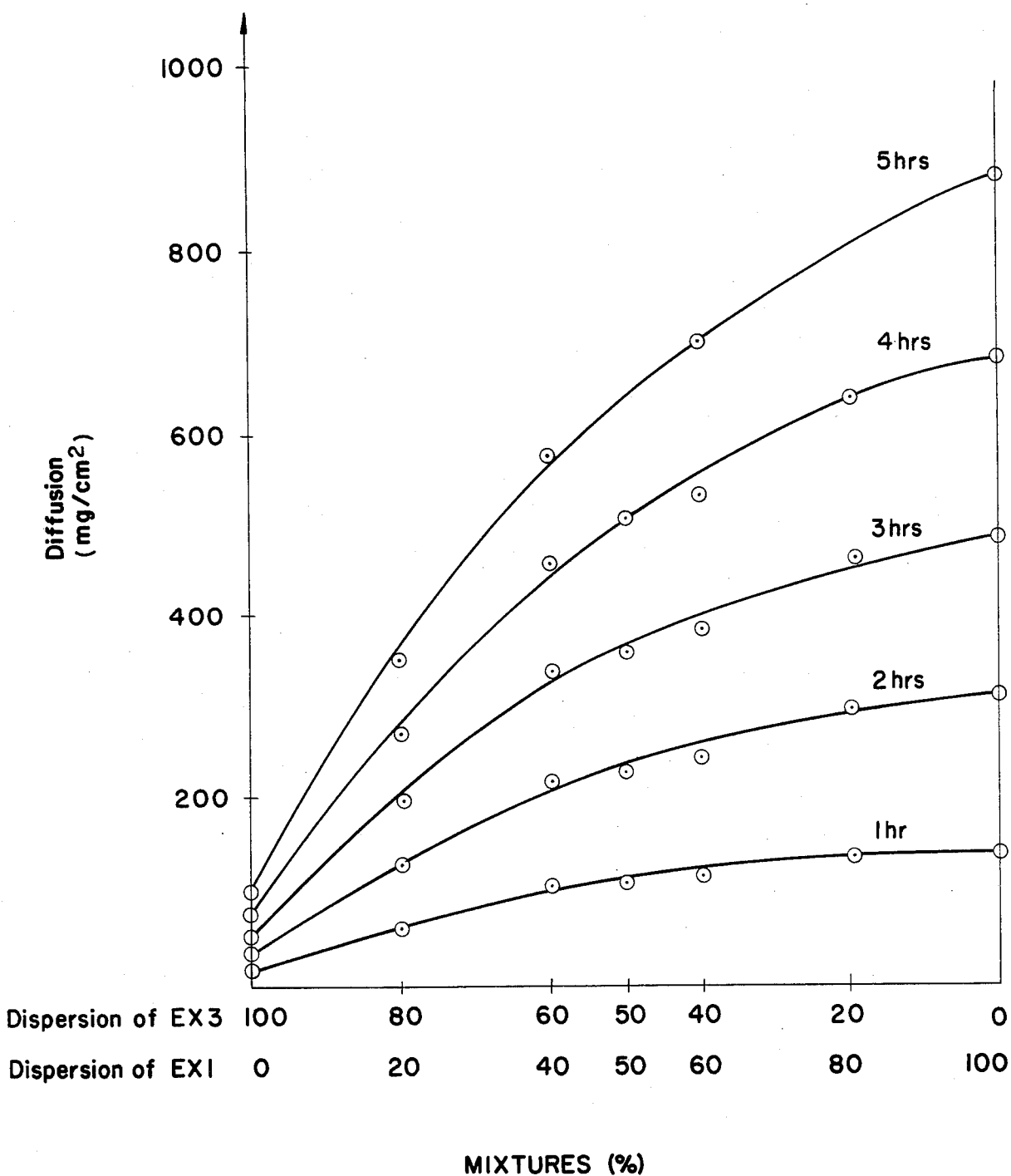

AQUEOUS COATING DISPERSIONS

This application is a continuation of application Ser. No. 937,430 filed Dec. 2, 1986 and now abandoned which in turn is a continuation of application Ser. No. 787,969 filed Oct. 16, 1985 and now abandoned.

The present invention relates to film-forming aqueous dispersions of coating and binder agents, to methods for making such dispersions, and to the use of such dispersions for coating pharmaceutical dosage forms, for the granulation of pharmaceutically active powders, and for the production of pharmaceutical films.

Aqueous coating dispersions for pharmaceutical dosage forms are known from published German patent application DOS No. 32 08 791 (corresponding to European patent publication No. 88,951). Such dispersions are prepared by reemulsifying a powdered emulsion polymer containing acid or basic groups in a water phase in which a small portion of the acid or basic groups is converted to the salt form by means of a base or an acid. By such a process, the original latex particles are isolated and, by salt formation on their surface, are hydrated and stably dispersed. Because of the content of acid or basic groups of the coating agent, the solubility or permeability to digestive fluids of the coatings produced therefrom on pharmaceutical dosage forms depends on the pH value of those fluids. This pH dependence may be desirable or undesirable, depending on the intended mode of action of the drug.

Coatings for pharmaceutical dosage forms having a permeability for dissolved active ingredients that is independent of the pH value of the surrounding aqueous medium can be produced from the dragée coating compositions described in German patent No. 1,617,751. These compositions contain a copolymer having quaternary ammonium salt groups and are dissolved in organic solvents such as alcohols, ketones, or esters. Because of their content of quaternary ammonium groups, it is not possible to produce such polymers by emulsion polymerization and to prepare a redispersible powder therefrom.

The object of the invention is to provide an aqueous coating dispersion for pharmaceutical dosage forms which forms a film upon drying and which gives water insoluble coatings having a diffusion permeability that is independent of the pH value of the surrounding medium.

It has been found that such a dispersion can be prepared by dispersing a powdered coating agent in an aqueous phase with stirring if the powdered coating agent being dispersed in the aqueous phase is a copolymer, capable of swelling in water but not soluble therein, of a monoethylenically unsaturated quaternary ammonium compound capable of free-radical polymerization and of at least one nonionic monoethylenically unsaturated comonomer capable of free-radical polymerization and forming a water insoluble homopolymer.

Typical dispersions of this type contain from 60 to 85 percent, based on their total weight, of an aqueous phase and from 40 to 15 percent by weight of a copolymer dispersed therein, said copolymer comprising from 5 to 20 percent, by weight of the copolymer, of said quaternary ammonium compound, from 95 to 70 percent of said nonionic comonomer, and, optionally, up to 20 percent of other unsaturated comonomers which are copolymerizable with said monomers.

The new coating dispersions contain no volatile combustible components and therefore can be dried without posing a fire or explosion hazard and without polluting the exhausted air with impurities, apart from water vapor, to form clear films as good as the coatings produced by organic solutions of the same copolymers. The films are insoluble in water at all pH values in the physiological range but are capable of swelling in water to the extent that water and pharmaceutically active substances dissolved therein are able to diffuse through them. Like the swelling capacity, the diffusion permeability of the films is independent of the pH value unless the solubility or diffusibility of the active substance itself varies with the pH value. The pH-independent permeability is due both to the quaternary ammonium salt groups, which, being salts of a strong base, are completely dissociated throughout the physiological pH range, and to the absence of other ionic groups whose pH-dependent dissociation would result in a pH-dependent diffusion permeability.

The new dispersions thus are suitable for the production of delayed action pharmaceutical preparations which release the enclosed active substance at the same diffusion rate, regardless of the prevailing pH value, in each region of the digestive tract during passage therethrough and, after having been completely extracted, are eliminated without decomposing. Such polymer films may form an envelope over a tablet, a dragée, a capsule, a particle of an active substance, or the matrix for a granulation, or a matrix table compressed therefrom, or may contain the active substance embedded in the polymer film. The envelope may have a thickness from 10 to 50 microns and, if desired, may form one layer of a multilayer coating. The production of coating films, coated pharmaceutical dosage forms, or granulations may be effected in the same manner as with other known aqueous coating dispersions. These are frequently modified prior to use with fillers or pigments such as talc or titanium dioxide, with plasticizers, and, if indicated, with odor- or taste-making additives.

A special advantage is that by mixing two dispersions containing different amounts of quaternary ammonium groups the processor of the coating dispersions is able to obtain any desired permeability, and hence release rate, between the limits applicable when the two components are used alone. Since even minor differences in the composition of the copolymers result in pronounced differences in the release rate, a broad range of delayed actions can be obtained just by mixing. For example, a coating produced from a copolymer of ethyl acrylate, methyl methacrylate, and methacryloxyethyltrimethylammonium chloride in a weight ratio of 60:35:10 applied to the paper membrane of a diffusion cell for measuring purposes, allowed 10.5 parts of phenylpropanolamine hydrochloride to diffuse through it over a period of five hours, whereas an otherwise identical coating produced from a copolymer with a weight ratio of 65:35:5 of the same monomer constituents resulted in the diffusion of only 1.2 parts of said active substance under the same conditions. Mixtures of the two dispersions, under the same test conditions gave diffusion values lying between the two extremes. The accompanying FIGURE shows the diffusion pattern over a five hour period. The good controllability of the diffusion rate and the substantially linear diffusion rate with each selected composition of the diffusion layer are apparent from the drawing. The coatings of pharmaceutical dosage forms behave similarly.

The nature, and particularly the amount, of the quaternary ammonium compound present in the copolymeric agent are important factors affecting diffusion behavior. N-vinylpyridinium salts are suitable polymerizable quaternary ammonium compounds, for example. Quaternary aminoalkyl esters or aminoalkylamides of acrylic or methacrylic acid are preferred. These correspond to the general formula

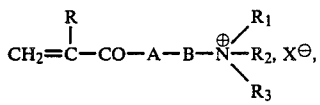

wherein
R is hydrogen or methyl;
A is oxygen or NH;
B is a linear or branched alkyl or is an alicyclic hydrocarbon, and more particularly has from 2 to 8 carbon atoms;
$R_1$, $R_2$, and $R_3$, taken alone, are the same or different alkyl or aralkyl, and more particularly are lower alkyl having from 1 to 4 carbon atoms, or are benzyl, or $R_1$ and $R_2$, taken together with the quaternary nitrogen atom, are piperidinium or morpholinium; and
$X^\ominus$ is a cation, preferably of an inorganic acid, particularly chloride, sulfate, or methosulfate.

Examples of this class of compounds are acryl- and methacryl-oxyethyltrimethylammonium chloride and methosulfate, benzyldimethylammoniumethylmethacrylate chloride, diethylmethylammoniumethyl-acrylate and -methacrylate methosulfate, N-trimethylammoniumpropylmethacrylamide chloride, and N-trimethylammonium-2,2-dimethylpropyl-1-methacrylate chloride.

As a rule, these monomers are used in an amount from 5 to 20 percent by weight of the copolymer. Adequate diffusion permeability cannot be obtained with lower amounts. Higher amounts render the copolymer water soluble. The preferred content ranges from 5 to 10 weight percent. The amount of these monomers is advantageously kept at such a level that the finely divided polymer in pure water will take up from 10 to 100, and preferably from 20 to 80, percent by weight of water by swelling. For mixing, two copolymers, for example, may be used, one of which takes up from 10 to 40 weight percent, and the other from 50 to 80 weight percent, of water.

Suitable nonionic comonomers forming water insoluble homopolymers are primarily the alkyl esters of acrylic acid and methacrylic acid, styrene and its homologs, vinyl esters, and vinyl chloride. For the purposes of this application, nonionic monomers include not only monomers which have no ionic groups (such as alkali metal carboxylate or sulfonate or tertammonium groups) in the molecule, but also monomers, which are unable to form such groups with bases or acids. Alkyl esters of acrylic acid and methacrylic acid having from 1 to 8 carbon atoms in the alkyl group are preferred.

The hardness and extensibility of the coating film and the lowest temperature at which film formation from the dispersion is possible are considerably influenced by this monomer component. Esters of acrylic acid will reduce the hardness of the film, increase its elasticity and extensibility, and lower the film forming temperature. Since acrylic acid esters and the higher alkyl esters of methacrylic acid usually result in films that are too soft and sticky when they are used as the sole nonionic comonomers, they are preferably used in combination with monomers which when used alone form harder homopolymers, for example styrene and the lower alkyl esters of methacrylic acid. These esters alone usually result in films that are too hard or in a film forming temperature that is too high. Higher alkyl groups (having more than 4 carbon atoms), or aryl groups, have a hydrophobizing effect and thus reduce the swelling capacity and diffusion permeability. Comonomers with such groups therefore should be used only when such an effect is intended.

The advantageous properties of the dispersions in accordance with the invention or of the coatings produced therefrom can be brought about with the two monomer components described above, that is the quaternary ammonium monomers and the nonionic monomers, alone. However, in many cases the composition of the copolymer may include other monomers without the aims of the invention being jeopardized. However, ionic monomers, as defined above, should preferably not be used in an amount greater than from 1 to 2 percent by weight of the copolymer. Small amounts of ionic monomers, such as acrylic acid or methacrylic acid or the amino monomers on which the quaternized monomers are based, occasionally are difficult to exclude as impurities of the starting monomers. Water soluble nonionic monomers such as acrylamide or methacrylamide, vinylpyrrolidone, or hydroxyalkyl esters of acrylic acid or methacrylic acid may appreciably influence the swelling and diffusion behavior but will not affect the pH independence of that behavior. The amount of such monomers should not be greater than 20 percent of the copolymer and is preferably less than 10 percent or even less than 5 percent. Hydroxyalkyl esters frequently prove deleterious and are best avoided altogether. Similarly, ethylenically polyunsaturated monomers, which would result in crosslinking, should not be used even in minor amounts.

The production of the copolymer is not part of the invention and may be carried out by any desired appropriate method. Bulk polymerization in the presence of a free radical-forming initiator dissolved in the monomer mixture is simplest. Another method is solution or precipitation polymerization in an organic solvent, the polymer formed then being isolated from the solvent. What is important in all cases is that the copolymer be obtained in the form of a fine powder, which in the case of bulk polymerization is accomplished by grinding and in the case of solution or precipitation polymerization by spray drying. The powder particles should be of a size that will pass through a screen having a clear mesh opening of 200 microns. Particle sizes ranging from under 20 to 50 microns are usable but are not very practical because of their tendency to dust.

As a rule, the mere dispersing of the powdered copolymer in water will not result in a stable film forming dispersion. Surprisingly, with prolonged stirring at elevated temperature, self-emulsifying particles of a size far below that of the powder particles used will form. Their average size (weight average) may range from 1 to 50 microns and preferably is between 10 and 20 microns. To obtain a stable dispersion of the copolymer, it will suffice to keep the powder particles suspended by stirring and to prevent the formation of a sediment. This can be accomplished by low to moderate stirring rates in the usual agitated vessels. Stirring should be continued until no sediment forms when the dispersion is allowed to stand. To obtain complete emulsification, a stirring time of at least 15 minutes, and preferably more than 20 minutes, for examples from 30 to 60 minutes, is usually required. There is no need to add emulsifiers. A limit is imposed on longer stirring times or higher stirring rates only by gradually increasing foaming.

The formation of the dispersion will be promoted if a plasticizer for the copolymer is added at the very beginning. Amounts of plasticizer ranging from 10 to 20 percent, based on the weight of the copolymer, will be effective during the dispersing process itself and improve the film forming capacity in the production of coatings. Nonvolatile additives having a molecular weight of generally under 1000 which are compatible with the copolymer and are physiologically safe are suitable for use as plasticizers. These are predominantly liquid substances or substances which solidify amorphously and melt readily, such as polyethylene glycols, citrates of lower alcohols, or fatty acid esters of sugar alcohols or their ethoxylation products, of which optionally ethoxylated sorbitan monooleate is the best known example.

Dispersions which without the addition of a plasticizer form films only at 40° C. or 50° C. will give clear and homogeneous coatings even from 0° C. to 20° C. when they incorporate a plasticizer.

The temperature required to form the dispersion depends on the hardness of the polymer and should be increased with increasing polymer hardness. Temperatures ranging from 50° C. to 100° C., and preferably from 60° C. to 80° C., will generally be appropriate. The ratio between the amount of powder and the amount of aqueous phase should be such that a dispersion readily forming a film is obtained. The film forming capacity under the conditions of commercial coating methods depends on the solids content of the dispersion. When the solids content is too low, a uniform film is not obtained or a disproportionately long drying time is required. As a rule, good film forming capacity is obtained when the copolymer represents from 15 to 40 weight percent and the aqueous phase from 85 to 60 weight percent of the dispersion.

Dispersions with a still higher solids content are difficult to prepare because of their increasing viscosity and are difficult to process for the same reason.

While stable dispersions may be produced, stored and marketed in large quantities, the processor will find it more advantageous to prepare dispersions of the powdered coating composition himself according to his short term needs. This makes it possible to use several copolymer powders with different swelling capabilities in the required mixing ratio depending on the delayed action desired in a given case and, in the same operation, to formulate the dispersion with plasticizers and other additives as required.

The application of coatings to pharmaceutical dosage forms by the use of the coating dispersions of the invention is conventionally effected by pan coating or air suspension methods. Powders or crystals of an active material can be granulated conventionally. The preferred use is the production of topcoats from 10 to 50 microns thick on pellets or granulations, which may be used to fill hard gelatin capsules for example. Moreover, the dispersions may be used to manufacture dermal or transdermal pharmaceutical dosage forms by embedding active substances in layers of film and applying the films to paper sheets or inert plastic foils, or by producing unsupported layers of film.

The dispersions should be processed at temperatures under 80° C. and generally not over 60° C. Temperatures under 40° C., for example between 20° C. and 30° C. are preferred. During manufacture, it should be endeavored to produce coatings or films which do not become tacky at temperatures up to 30° C. to 35° C.

A better understanding of the present invention and of its many advantages will be had by referring to the following specific examples, given by way of illustration.

EXAMPLE 1

350 g of water were heated to 65° C. in a flask with stirring and 150 g of a finely ground bulk polymer comprising 60 parts by weight of methyl methacrylate, 30 parts of ethyl acrylate and 10 parts of trimethylammoniumethylmethacrylate chloride were introduced into it over a period of about 10 minutes. The polymer powder has previously been passed through a screen with a clear mesh opening of 0.2 mm. The stirring rate was controlled so that the particles were unable to settle on the bottom or walls of the flask. The temperature ranged from 65° C. to 75° C. By the end of 2 hours, a milky, slightly viscous dispersion had formed, which was passed through a screen with a clear mesh opening of 0.1 mm. The oversize was less than 3 g, so that more than 98% of the polymer had been dispersed. The solids content of the dispersion was 30.1%.

100 g of the dispersion were mixed with 3 g of triethyl citrate as a plasticizer. Above a minimum film forming temperature of 17° C., clear, readily stripped films formed when the dispersion was brush coated onto a PVC plate.

EXAMPLE 2

300 g of an aqueous dispersion prepared as described in Example 1 and having a solids content of 30% were mixed with 800 g of a pigment suspension of 125 g of talc, 55 g of titanium dioxide, 25 g of yellow lacquer E 104, 25 g of polyethylene glycol 6000, and 570 g of water and were then diluted with a further 500 g of water so that a total solids content of 20% was obtained in the lacquer pigment suspension. 10 kg of tablets (diameter, 7 mm; height, 3.5 mm; weight, 140 mg each) were preheated to about 30° C. in a steel coating cylinder having a diameter of 50 cm by blowing in warm air, and a fine jet from an air pressure spray gun having a nozzle 1.5 mm in diameter was directed at an air pressure of about 1 bar onto the cores rotating in the coating cylinder. The spraying rate was held at 25–30 g/minute while drying air of a temperature between 40° C. and 60° C. was being continuously blown in. Under these operating conditions, the tablet cores had a surface temperature of about 25° C. On completion of spray coating after 90 minutes, warm air was blown in for another 5 minutes while the cylinder was slowly rotated. The coated tablets were then spread out on filter paper and allowed to dry further in air overnight. A uniformly colored, glossy coating was so obtained. The coated tablets are dust-free and easy to swallow. In water, artificial gastric fluid, and aqueous buffer solutions, rapid swelling and lifting of the coating film occurs within 10 minutes, so that the ingredients of the tablet are released quickly.

EXAMPLE 3

350 g of water were mixed in a 500 ml round-bottomed flask with 45 g of "Tween" (sorbitan monooleate ethoxylate) and heated to 80° C. to give a clear solution. Then 50 g of a copolymer comprising 65 parts of methyl methacrylate, 30 parts of ethyl acrylate, and 5 parts of trimethylammoniumethylmethacrylate chloride, in the form of a coarse granulation with a particle size of about 1 to 2 mm, were introduced into the solution. The stirring rate was controlled so that no particles were able to deposit on the walls. After one hour's stirring, another 50 g of the polymer were added, and this addition was repeated after still another hour's stirring at 80° C. The mixture was then stirred for another 5 hours at 80° C. and allowed to cool gradually overnight. The milky dispersion was passed through an 0.1 mm screen. The oversize was less than 5 g. The solids content of the dispersion was 29%.

100 g of this dispersion were mixed with 3 g of triethyl citrate and, upon drying of a layer formed therefrom, gave a clear but still brittle film. When another 3 g of the citrate ester were added, a flexible film was obtained, the minimum film forming temperature being 2° C.

Determination of the particle size distribution by means of an ultracentrifuge showed that the average particle size ranged from 150 to 200 nm. A few particles in the one micron size range were also visible.

EXAMPLE 4

350 g of water were heated to 60° C. and 5 g of triethyl citrate was dissolved therein with stirring. Then 50 g of a spray dried polymer comprising 60 parts by weight of methyl methacrylate, 30 parts of ethyl acrylate, and 10 parts of trimethylammoniumethylmethacrylate chloride were stirred into the solution. Within 90 minutes a milky dispersion formed and was cooled to room temperature with stirring.

EXAMPLE 5

400 g of a theophylline powder having a particle size under 0.2 mm, together with 160 g of secondary calcium phosphate, were uniformly wetted in a kneader with 400 g of a dispersion prepared as described in Example 3 and then diluted to 15% solids content. This mixture was granulated on a granulator having a screen with a clear mesh opening of 1.5 mm. The resulting granulation was dried in a hot air oven at 100° C. to a residual moisture of less than 2 percent, then again passed through a 1.5 mm screen, and mixed in a double cone mixer with 6.6 g of talc and 3.6 g of magnesium stearate as a lubricant. This granulation was compressed into tablets each having a diameter of 12 mm and a total weight of 500 mg, so that the content of active ingredient was 400 mg per tablet. In a release test run in a paddle apparatus conforming to USP XX (Apparatus No. 2), these tablets showed a release of active ingredient delayed for 6 hours.

EXAMPLE 6

1.5 kg of microdragées having a particle diameter from 0.5 to 1.2 mm and containing 8 percent of chlorophenamine maleate as an active ingredient were fluidized in an air suspension apparatus ("Uniglatt", made by Glatt of Binzen, West Germany) in a stream of hot air at 50° C. and then spray coated over a period of 80 minutes by means of an air pressure spray gun having a nozzle diameter of 1 mm at a spraying pressure of 1.8 bar with a mixture of 500 g of a dispersion prepared as described in Example 3 and having a solids content of 30 percent, 30 g of triethyl citrate, 75 g of talc, and 700 g of water as a diluent. After 80% of the above formulation, which corresponds to a coating which is 8 percent of the initial weight of the pellets, had been deposited, samples were taken and analyzed in a paddle apparatus conforming to USP XX, Apparatus 2. The same was done after the amount of coating was 10 percent of the initial weight of the pellets. The test showed a delayed sustained release of the active ingredient with the following values:

| | 8% coating deposit | |
|---|---|---|
| 1 hour | 7.5% | pH 1.5 |
| 2 hours | 28.5% | pH 2.1 |
| 3 hours | 55% | pH 5.5 |
| 4 hours | 73% | pH 6.5 |
| 5 hours | 84% | pH 6.7 |
| 6 hours | 92% | pH 6.8 |
| | 10% coating deposit | |
| 1 hour | 1.5% | pH 1.5 |
| 2 hours | 8.0% | pH 2.1 |
| 3 hours | 19.5% | pH 5.5 |
| 4 hours | 39.5% | pH 6.5 |
| 5 hours | 59% | pH 6.7 |
| 6 hours | 71% | pH 6.8 |

Mixtures of artificial gastric fluid and artificial intestinal fluid conforming to the British Pharmacopoeia were used as solvents, whereby the pH values indicated, which increase from one hour to the next, resulted.

EXAMPLE 7

Mixtures of the dispersions prepared as described in Example 1 and 3, each having a solids content of 30%, were prepared in the ratios 8:2, 6:4, 5:5, 4:6, and 2:8. The unmixed dispersions were also analyzed. A sheet of paper about 15 microns thick was first wetted with water and excess liquid was removed with a rubber roller. Sufficient dispersion was then deposited on the paper so pretreated that a film layer 20 microns thick formed. After complete drying, the coated paper was inserted in a 12 cm² diffusion cell of a Sartorius resorption apparatus, model SM 16750, and flushed from the coated side with a 36% solution of phenylpropanolamine hydrochloride in water and from the other side with an isotonic phosphate buffer (according to Hagers Handbuck II, Suppl. Vol. I, p. 125) having a pH of 6.0. The amount of active substance diffusing through the coating film was then monitored spectrophotometrically at 262 nm with respect to time and the points of measurement were entered in the diagram of FIG. 1 after 1, 2, 3 4 and 5 hours as a function of the mixing ratio of the two dispersions. It was found that the dispersion prepared as described in Example 3 yields films of very low permeability while the films produced from the dispersion prepared as described in Example 1 exhibit very high permeability. The results obtained with the various mixtures fall between these two extremes so that such a diagram can be used to determine the optimum mixing ratio for a given active substance in order to match the release rate to therapeutic requirements.

EXAMPLE 8

10 g of a 10% solution of chlorophenamine maleate in water were mixed with 100 g of a dispersion prepared as described in Example 3 and having a 27 percent solids content. 6 g of triethyl citrate were added to the mixture as a plasticizer. Sufficient dispersion was then spread coated onto paper, as described in Example 7, to form a film about 115 microns thick. This film was tested for release of the active substance in a Sartorius resorption apparatus as described in Example 7, except that only the film side was rinsed with buffer. It was found that there was a delayed release of the active ingredient from the film over a period of more than 72 hours.

In following Examples 9-16, in each case 350 g of water were warmed to 60° C. and, in each case, 50 g of finely divided polymer powder were added with stirring and further heating. Stirring was continued until the formation of a uniform dispersion. The polymer composition (in parts by weight) and the conditions of dispersion are given below for each example.

EXAMPLE 9

The following ground bulk polymer was dispersed over a period of two hours at 90° C.:
60 parts of methyl methacrylate,
30 parts of ethyl acrylate, and
8 parts of 2-trimethylammoniumethyl-methacrylate methosulfate.

EXAMPLE 10

The following spray dried solution polymer was dispersed over a period of two hours at 80° C.:
60 parts of methyl methacrylate,
35 parts of ethyl acrylate, and
5 parts of diethylmethylammonium-ethyl-methacrylate methosulfate.

EXAMPLE 11

The following ground bulk polymer was dispersed over a period of three hours at 85° C.:
70 parts of methyl methacrylate,
20 parts of ethyl acrylate, and
10 parts of trimethylammoniumethyl-acrylate chloride.

EXAMPLE 12

The following ground bulk polymer was dispersed over a period of three hours at 85° C.:
50 parts of methyl methacrylate,
35 parts of ethyl acrylate, and
15 parts of trimethylammoniumpropylmethacrylamide chloride.

EXAMPLE 13

The following spray dried emulsion polymer was dispersed over a period of three hours at 80° C.:
50 parts of methyl methacrylate,
38 parts of ethyl acrylate, and
12 parts of trimethylammonium-2-dimethylpropyl-1-methacrylate chloride.

EXAMPLE 14

The following ground bulk polymer was dispersed over a period of three hours at 70°-85° C.:
40 parts of methyl methacrylate,
40 parts of ethyl acrylate, and
20 parts of 2-benzyldimethylammoniumethylmethacrylate chloride.

EXAMPLE 15

The following spray dried emulsion polymer was dispersed over a period of three hours at 85° C.:
40 parts of methyl methacrylate,
30 parts of butyl acrylate,
10 parts of octadecylmethacrylate, and
20 parts of trimethylammonium-2,2-dimethylpropyl-1-methacrylate chloride.

EXAMPLE 16

The following ground bulk polymer was dispersed over a period of two hours at 90° C.":
40 parts of methyl methacrylate,
40 parts of ethyl acrylate, and
18 parts of trimethylammoniumcyclohexylmethacrylate chloride.

What is claimed is:

1. The method of making a pharmaceutical dosage form which comprises the steps of
(A) preparing a polymer dispersion by dispersing particles of a preformed dry powdered copolymer in an aqueous phase by stirring at an elevated temperature until no sediment forms when said dispersion is allowed to stand, whereby self-emulsifying dispersed particles smaller than said powder particles are formed, said aqueous medium consisting essentially of water or of water and a pharmaceutically acceptable plasticizer for said copolymer, said copolymer being a water swellable but water insoluble copolymer consisting essentially of
(1) a monoethylenically unsaturated quaternary ammonium compound selected from the group consisting of N-vinyl pyridinium salts and quaternary aminoalkyl esters and quaternary aminoalkyl amides of acrylic acid of methacrylic acid of the formula

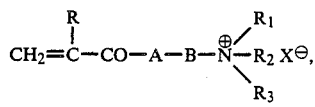

wherein
R is hydrogen or methyl;
A is oxygen or —NH—;
B is linear or branched alkyl or an alicyclic hydrocarbon;
$R_1$, $R_2$, and $R_3$, taken alone, are the same or different alkyl or aralkyl, or $R_1$ and $R_2$, taken together with the quaternary nitrogen atom, are piperidinium or morpholinium; and
(2) at least one nonionic monomer, and
(B) applying said polymer dispersion to a core comprising a pharmaceutically active substance and drying said dispersion.

2. A method for making a granulation of a pharmaceutically active powder which comprises the steps of
(A) preparing a polymer dispersion by dispersing particles of a preformed dry powdered copolymer in an aqueous phase by stirring at an elevated temperature until no sediment forms when said dispersion is allowed to stand, whereby self-emulsifying dispersed particles smaller than said powder particles are formed, said aqueous medium consisting essentially of water or of water and a pharmaceutically acceptable plasticizer for said copolymer, said copolymer being a water swellable but water insoluble copolymer consisting essentially of
(1) a monoethylenically unsaturated quaternary ammonium compound selected from the group consisting of n-vinyl pyridinium salts and quaternary aminoalkyl esters and quaternary aminoalkyl amides of acrylic acid or of methacrylic acid of the formula

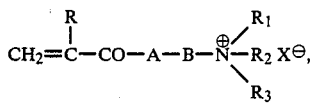

wherein
R is hydrogen or methyl;
A is oxygen or —NH—;
B is linear or branched alkyl or an alicyclic hydrocarbon;
$R_1$, $R_2$, and $R_3$, taken alone, are the same or different alkyl or aralkyl, or $R_1$ and $R_2$, taken together with the quaternary nitrogen atom, are piperidinum or morpholinium; and
(2) at least one nonionic monomer, and
(B) coating said powder with said polymer dispersion and drying said dispersion.

3. The method for making a film layer having a therapeutically active substance embedded therein which comprises the steps of
(A) preparing a polymer dispersion by dispersing particles of a preformed dry powdered copolymer in an aqueous phase by stirring at an elevated temperature until no sediment forms when said dispersion is allowed to stand, whereby self-emulsifying dispersed particles smaller than said powder particles are formed, said aqueous medium consisting essentially of water or of water and a pharmaceutically acceptable plasticizer for said copolymer, said copolymer being a water swellable but water insoluble copolymer consisting essentially of
(1) a monoethylenically unsaturated quaternary ammonium compound selected from the group consisting of N-vinyl pyridinium salts and quaternary aminoalkyl esters and quaternary aminoalkyl amides of acrylic acid or of methacrylic acid of the formula

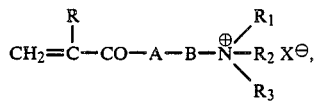

wherein
R is hydrogen or methyl;
A is oxygen or —NH—;
B is linear or branched alkyl or an alicyclic hydrocarbon;
$R_1$, $R_2$, and $R_3$, taken alone, are the same or different alkyl or aralkyl, or $R_1$ and $R_2$, taken together with the quaternary nitrogen atom, are piperidinum or morpholinium; and
(2) at least one nonionic monomer, and
(B) mixing said polymer dispersion with said active substance and drying said dispersion in the form of a layer.

* * * * *